United States Patent [19]

Bauer et al.

[11] Patent Number: 4,768,969
[45] Date of Patent: Sep. 6, 1988

[54] ELECTRICAL CONNECTOR

[75] Inventors: Ronald W. Bauer, Elizabeth; Robert A. Weiss, Aurora, both of Colo.

[73] Assignee: C. R. Bard, Inc., Murray Hill, N.J.

[21] Appl. No.: 60,116

[22] Filed: Jun. 9, 1987

Related U.S. Application Data

[63] Continuation of Ser. No. 838,316, Mar. 10, 1986, abandoned.

[51] Int. Cl.⁴ .............................................. H01R 9/07
[52] U.S. Cl. ................................... 439/260; 439/261; 439/267; 439/372; 439/499; 439/725
[58] Field of Search ................ 339/61 R, 61 M, 75 R, 339/75 M, 75 MP, 91 R, 17 F, 176 MF; 128/798, 800, 801; 439/260, 261, 263, 372, 492, 499, 592, 593, 725, 267

[56] References Cited

U.S. PATENT DOCUMENTS

| 3,437,979 | 4/1969 | Beaudion | 339/95 |
| 3,671,924 | 6/1972 | Nagano | 339/95 D |
| 3,699,968 | 10/1972 | Bolduc | 128/303.13 |
| 3,817,253 | 6/1974 | Gonser | 339/261 |
| 3,842,394 | 10/1974 | Bolduc | 339/75 R |
| 4,061,408 | 12/1977 | Bast et al. | 339/75 R |
| 4,304,453 | 12/1981 | Grunwald | 339/75 R |
| 4,477,137 | 10/1984 | Ayer | 339/17 F |

FOREIGN PATENT DOCUMENTS

| 698229 | 11/1940 | Fed. Rep. of Germany . |
| 264135 | 4/1929 | Italy . |
| 647781 | 2/1979 | U.S.S.R. . |
| 807417 | 3/1981 | U.S.S.R. . |

Primary Examiner—J. Patrick McQuade
Attorney, Agent, or Firm—John R. Ley

[57] ABSTRACT

An electrical connector achieves improvements in connecting a patient plate to an electrosurgical generator. The connector is preferably of the lever operated type, and electrical contacts are connected on the lever and connected within a passageway internally in a housing of the connector. A tongue portion of the patient plate is inserted in the passageway. Upon closure of the lever, the contacts on the lever extend into the passageway above the lower contacts to mechanically contact and retain the tongue portion between the contacts and to electrically contact the tongue portion by which to conduct current to the patient plate. A recess is formed in the lower marginal area of the passageway and a retaining structure on the lever member extends into the passageway to deform the tongue portion into the indention. The electrical contacts are spacially separated and electrically interconnected to provide an upper and lower electrical contact point for the tongue conductor which is electrically insulated from another spacially separated upper and lower electrical contact point.

17 Claims, 6 Drawing Sheets

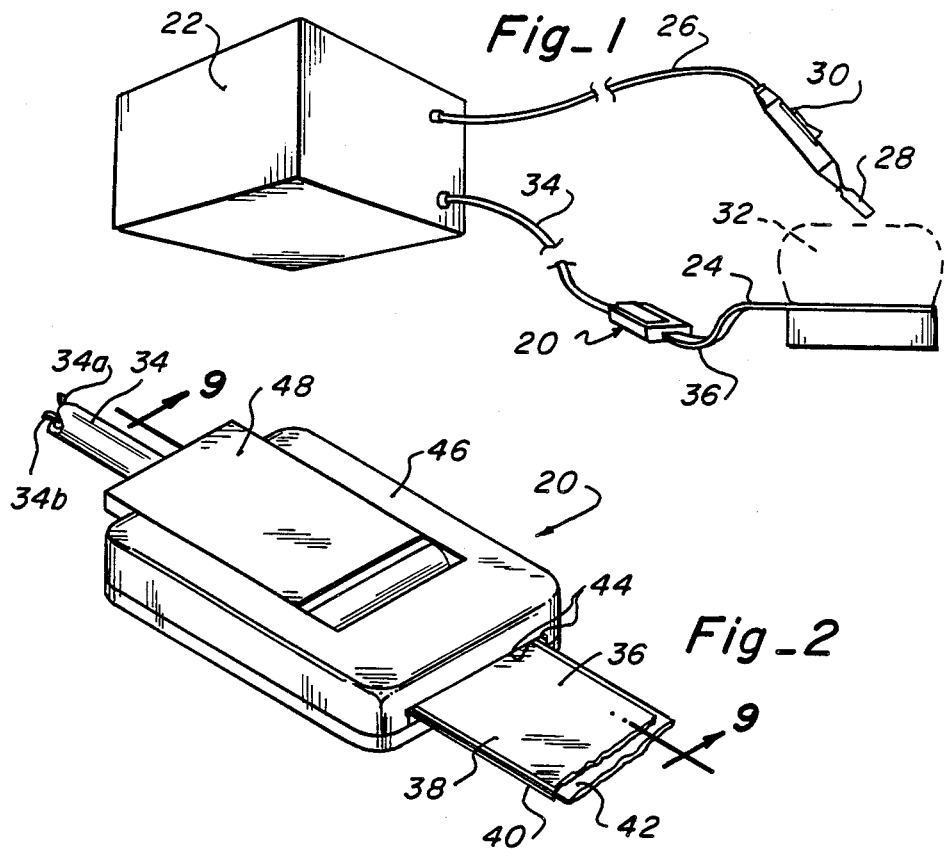
Fig_1
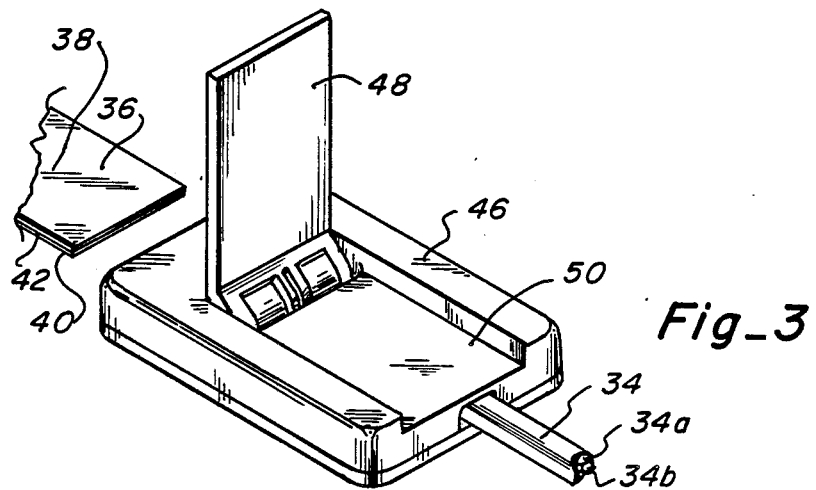
Fig_2
Fig_3

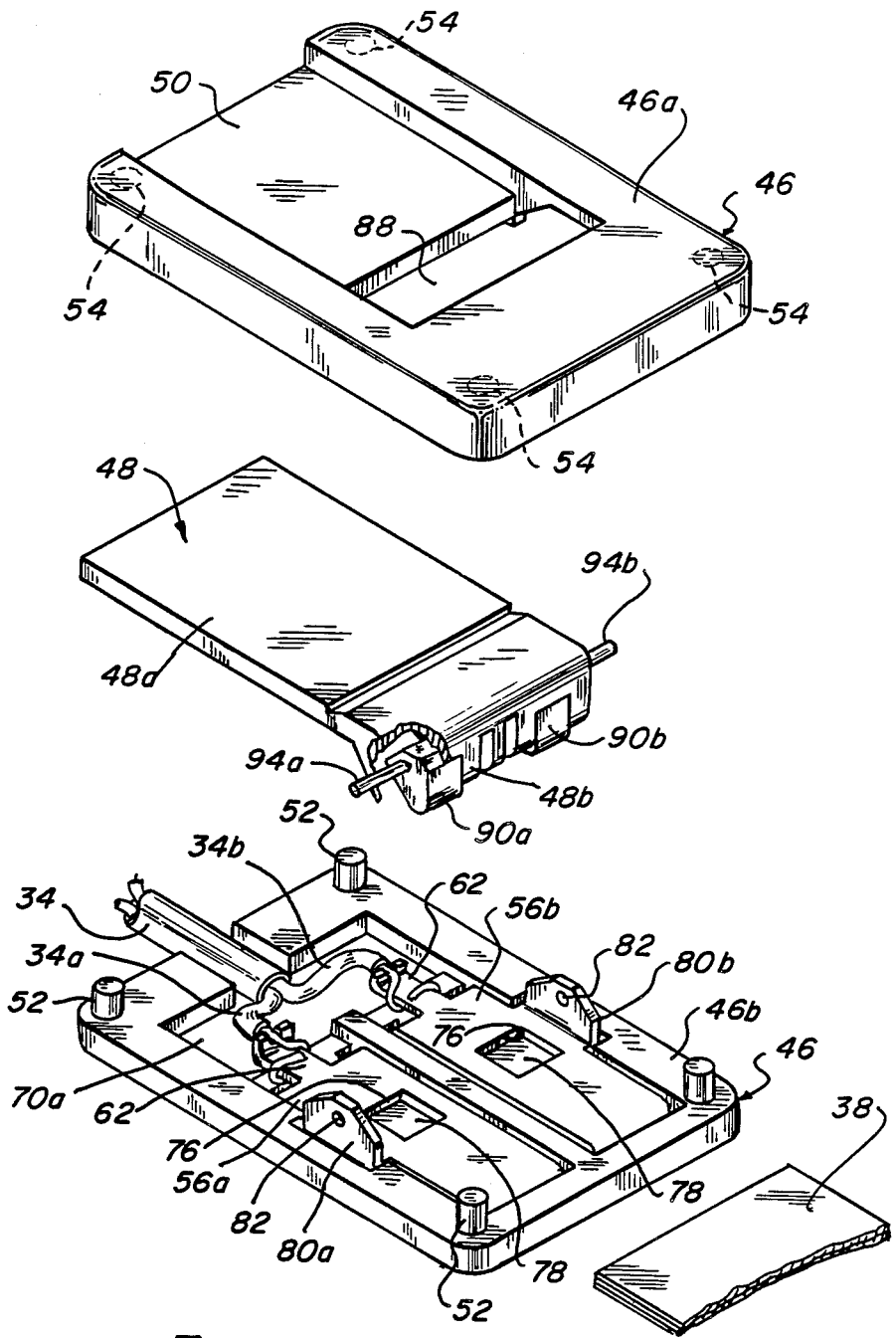
Fig_4

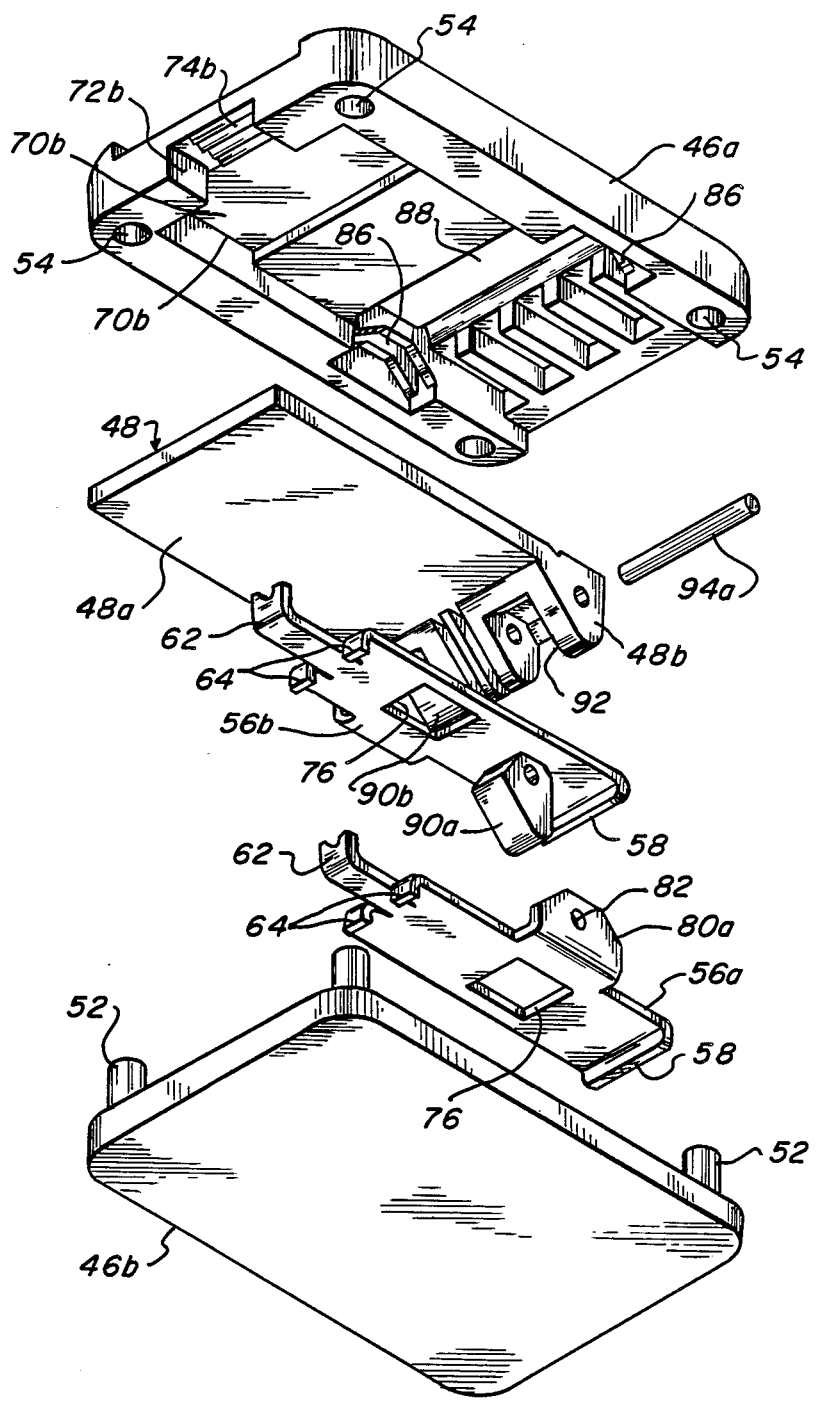
Fig_5

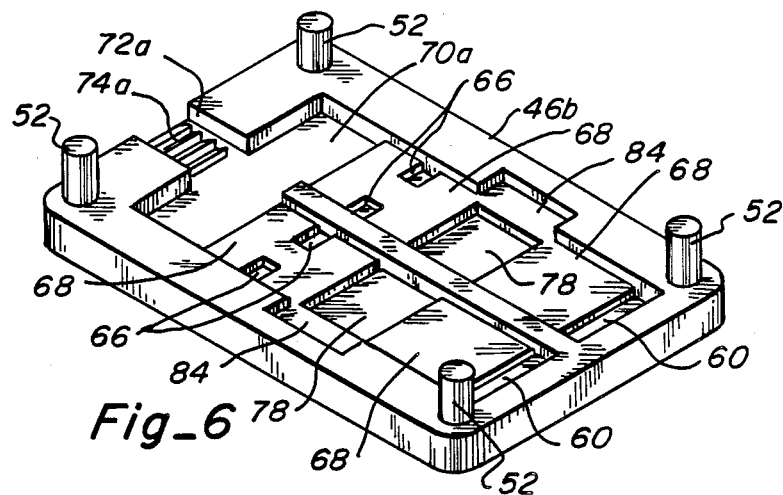

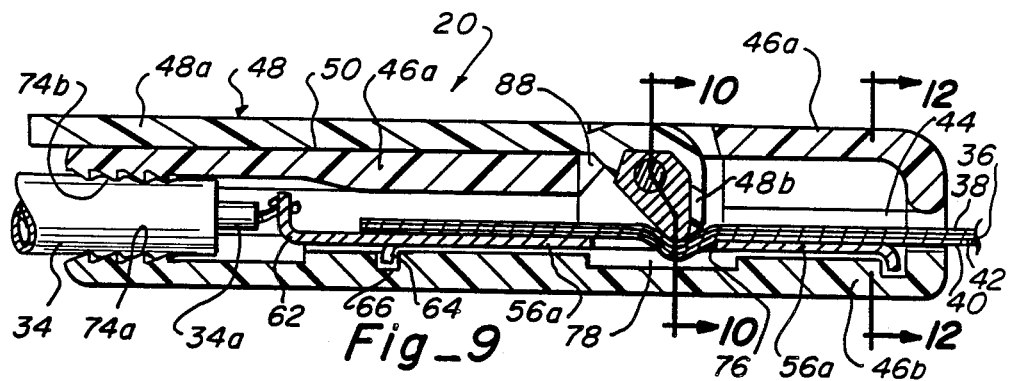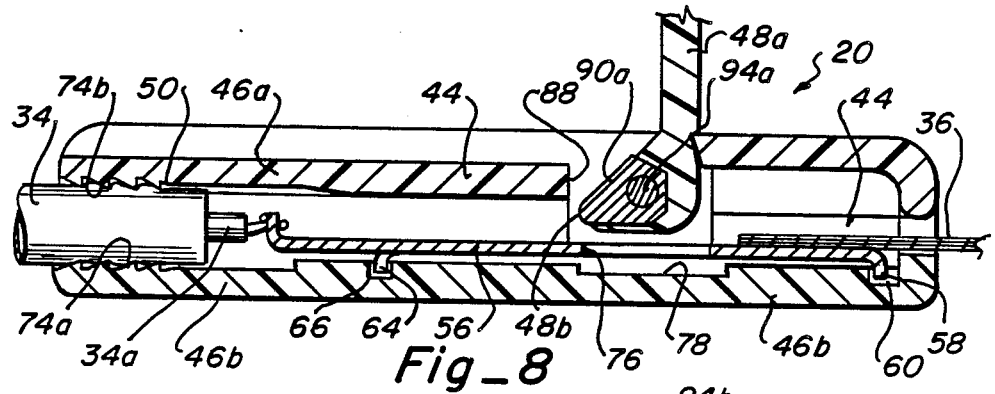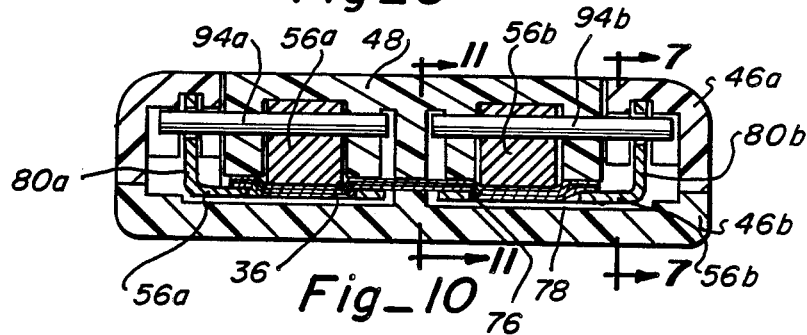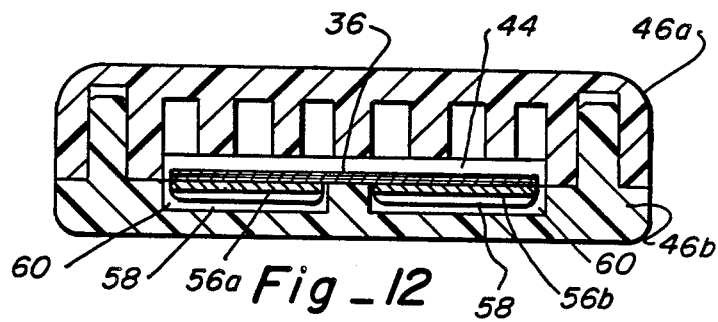

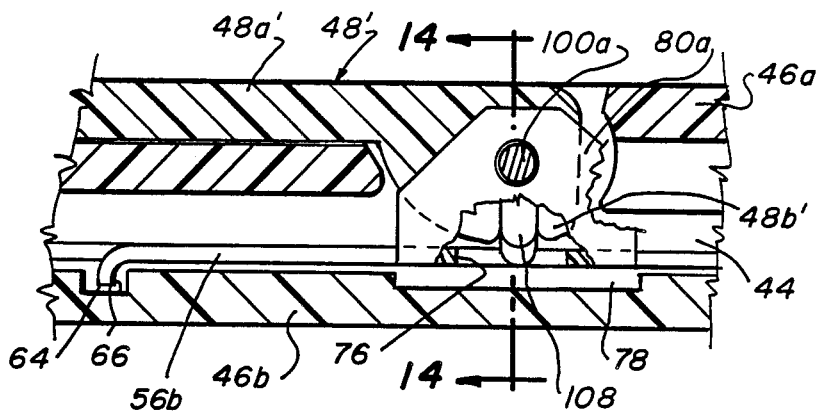
Fig_13
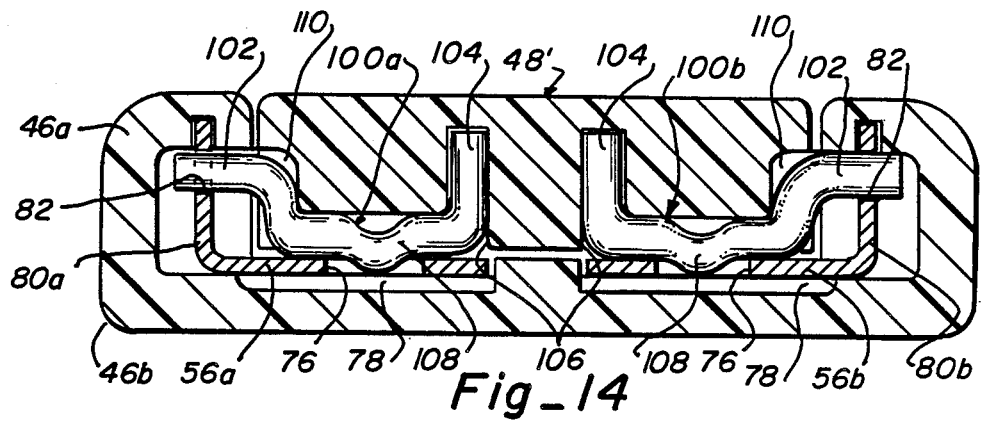
Fig_14
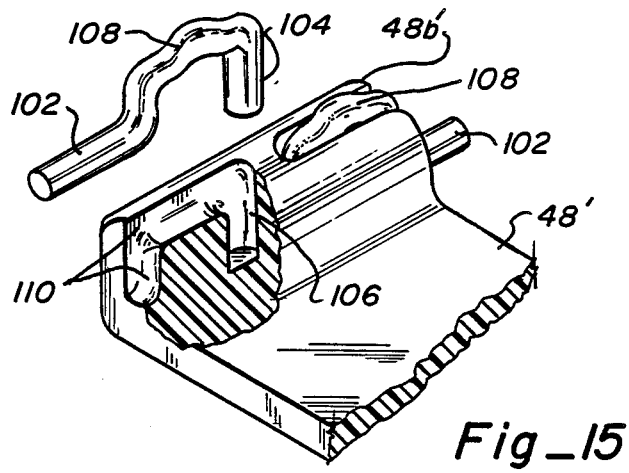
Fig_15

ELECTRICAL CONNECTOR

This application is a continuation of application Ser No. 838,316, filed Mar. 10, 1986, and now abandoned.

This invention relates to an electrical connector useful for establishing a selective electrical connection to a tongue-like electrical conductor. More specifically, the present invention relates to improvements in electrical connectors which are used in electrosurgery for selectively connecting the return conductor of an electrosurgical generator to a patient plate or grounding pad.

BACKGROUND OF THE INVENTION

In electrosurgery, high-frequency electrical energy is generated by an electrosurgical generator and conducted to an active electrode. A surgeon manipulates the active electrode over the tissue of the patient. Depending upon the characteristics of the electrical energy entering the tissue from the active electrode, cutting, cutting with hemostasis and coagulation surgical effects can be created. The electrical current flows from the surgical site through the patient's body to a patient plate or electrode, also known as a grounding pad. The patient plate is of relatively large dimensions to conduct current from a relatively large area of the patient's body. Due to the relatively large conductive surface and the relatively low current density, the energy concentration at the patient plate is insufficient to create tissue burning or other destructive effects at the patient plate.

Establishing and maintaining a proper electrical connection of the patient plate in the electrosurgical circuit is very important to the safety of the patient. Should the electrical connection between the patient and the patient plate, or between the patient plate and the electrosurgical generator become disrupted or discontinuous, earth ground current leakage paths from the patient to the surrounding equipment such as the surgical table can occur. The leakage paths are random and usually involve relatively low cross-sectional, high density currents. Burns to the patient can occur as a result of these leakage paths.

Because of the possibility for unintentional patient burns, patient plate continuity sensing circuits have been incorporate in many electrosurgical generators. The patient plate sensing circuits electrically sense the electrical connection of the patient plate to the return conductor of the electrosurgical generator. Should a break in continuity be sensed, the electrosurgical generator immediately terminates its electrical output. The most typical patient plate continuity sensing arrangement involves connecting two return cable conductors at separate locations to the patient plate, and sensing the continuity through the patient plate between the two conductors. This sensing arrangement determines if the patent plate is properly connected to the return conductor of the generator.

Disposable patient plates are typically used in electrosurgery. An electrical connector is therefore employed on the end of the generator return conductor in order to selectively connect to and disconnect from the disposable patient plates. The electrical connector accepts a conductive tongue formed on the disposable patient plate. The tongue of the patient plate is inserted into the connector, and the connector is manually manipulated to retain the tongue during the electrosurgery. The connector establishes the electrical connection through which the continuity sensing current flows and the current path for the high frequency electrosurgical current.

The connector should also create sufficient retention force on the tongue of the patient plate to restrain it against accidental disconnection. Accidental disconnection might occur as a result of someone tripping over the return conductor during the surgical procedure, for example. The patient plate is usually so sufficiently restrained against the patient by a conductive adhesive gel, that a large force on the return conductor might separate the connector from the patient plate. Upon disconnection and before the continuity sensing safety circuit can terminate the output current from the generator, momentary leakage paths to earth ground can cause patient burns. Of course if the generator does not include a continuity sensing safety circuit, the earth ground leakage paths can result in substantial burns and tissue destruction.

To resist accidental disconnection, one prior approach used in disposable patient plates has been to form holes or other special retaining configurations in the tongue of the patient plate. Such special retaining configurations are not universally employed in all types of electrosurgical equipment. Consequentially special patient plates must be used with particular equipment. Generally speaking, more universally usable equipment is generally preferred because it is available from multiple different sources. Accordingly, special retaining devices on patient plates and the corresponding retaining arrangements used in connector clamps are generally not favored.

The patient plate connector should also be relatively convenient for use. An attendant should be able to easily connect the connector to the tongue of the patient plate by holding the connector in one hand and the patient plate in the other hand. The attendant should be able to physically sense the proper operation of the connector in establishing an electrical and mechanical connection to the patient plate. The electrically conductive elements of the connector should be substantially insulated from the outside environment to avoid spaces and openings through which the relatively high voltage electrical energy can be conducted to the external environment. Since the patient plate and the attached connector are sometimes placed fully under the patient laying prone on a table, the connector should be of a configuration which does not physically injure the patient or of a configuration which provides an opportunity for high density current to travel from the patient into the connector by avoiding the larger surface area of the patient plate.

It is with respect to these considerations and others, that the improvements of the present invention have evolved.

BRIEF SUMMARY OF THE INVENTION

The electrical connector of the present invention provides improvements in establishing a selective electrical connection to a tongue-like conductor or portion of, for example, the patient plate. The connector includes a housing which defines a passageway into which the tongue conductor can be inserted. A lever member is pivotable with respect to the housing to move between opened and closed positions. Means for contacting and mechanically retaining the tongue conductor within the housing becomes operative when the lever is in the closed position. Moving the lever to the open position releases the mechanical connection to allow withdrawal of the tongue conductor. A pair of upper electrical contact means or a pair of lower contact means, or both, are located within the housing. Each of the upper and each of the lower contact means are positioned in a spacially separated and electrically insulated relationship with one another, and the contact means electrically contact the tongue conductor at spacially separated positions. Means within the housing electrically connects the separated contact means to each of the two electrical return cable conductors to enable sensing current to be conducted through the tongue conductor between the separated contact means.

The retention means operatively deflects or deforms the tongue conductor portion into a recess within the connector when the lever is in the closed position. The curvature of the deflected tongue portion creates forces tending to prevent the accidental separation of the tongue conductor from the connector. In one embodiment. the upper contact means forms a part of the means for contacting and mechanically retaining the tongue conductor. An improved arrangement is therefore provided for mechanically and electrically connecting the tongue conductor, to avoid intermittent continuity and hence risks of patient burns as a result of current flowing through earth ground leakage paths. Because the presence of the tongue conductor in the connector is required in order to achieve a mechanical and electrical connection to the patient plate, a proper electrical and mechanical connection can be manually sensed when the lever is moved to the closed position. The force created by deforming the tongue conductor preferably induces a torque on the lever member tending to maintain the lever in the closed position.

The invention itself is defined in the appended claims. Preferred embodiments of the invention are described in greater detail in the accompanying drawings and the following description of the preferred embodiments.

BRIEF DESCRIPTION OF THE DRAWINGS

FIG. 1 is a generalized perspective view of an electrosurgical generator, a supply conductor, an active electrode, a patient plate, a return conductor, and the electrical connector of the present invention which connects the return conductor to the patient plate.

FIG. 2 is an enlarged perspective view of the connector of the preaent invention shown in FIG. 1. FIG. 2 illustrates a lever member of the connector in the closed or locked position.

FIG. 3 is a perspective view of the connector shown in FIG. 2 but illustrated from a perspective point on the opposite side of the connector from that perspective point of FIG. 2. FIG. 3 illustrates the lever member of the connector in an open or unlocked position.

FIG. 4 is a top perspective view of the connector of the present invention illustrating its elements in an exploded relationship, with certain portions broken away for clarity.

FIG. 5 is a bottom perspective view of the connector of the present invention illustrating its elements in an explored relationship.

FIG. 6 is a perspective view of a lower housing portion of the connector as shown in FIG. 4.

FIG. 7 is a side elevational view of the connector shown in FIG. 2, with a portion broken out generally in the plane of line 7—7 as shown in FIG. 10.

FIG. 8 is an enlarged vertical section view taken in the plane of line 9—9 shown in FIG. 2, but illustrating certain elements of the connector in an open or unlocked position.

FIG. 9 is an enlarged vertical section view taken substantially in the plane of line 9—9 of FIG. 2.

FIG. 10 is a transverse section view taken substantially in the plane of line 10—10 of FIG. 9.

FIG. 11 is a section view taken substantially in the plane of line 11—11 of FIG. 10.

FIG. 12 is another transverse sectional view taken substantially in the plane of line 12—12 of FIG. 9.

FIG. 13 is an enlarged partial section view of another embodiment of the connector taken generally in a middle location of the connector, but illustrating an alternative arrangement of electrical contact means connected to the lever member.

FIG. 14 is a section view taken substantially in the plain of line 14—14 of FIG. 13.

FIG. 15 is a perspective view of the pivoted end of the lever member of the connector shown in FIGS. 13 and 14, shown inverted and in which the contact means connected to the lever member has been shown in an exploded relation.

DESCRIPTION OF PREFERRED EMBODIMENTS

The electrical connector of the present invention is shown in FIG. 1 as used in a typical electrosurgical arrangement. The connector is reference 20 and is used in conjunction with an electrosurgical generator 22 and a patient plate 24. The electrosurgical generator 22 supplies high frequency current over a supply conductor 2 to an active electrode 28. The active electrode 28 is connected to a pencil-like device 30 which the surgeon manipulates over the tissue 32 of a patient. The electrical energy enters the tissue 32 from the active electrode 28 and creates the desired electrosurgical effect. The current flows through the tissue 32 to the patient plate 24. The connector 20 electrically connects the patient plate 24 to a return conductor 3 of the electrosurgical generator 22. An electrical circuit is established through the generator 22 and not through earth ground, which is important in avoiding patient plate burns. Two cable conductors 34a and 34b of the return conductor 34 are used for establishing the sensing current path for the typical continuity sensing arrangement of the typical electrosurgical generator.

The patient plate includes a typical tongue conductor or portion 36 illustrated in FIG. 2. The tongue conductor 36 includes upper and lower conductive foils 38 and 40, respectively, by which electrical energy is conducted to and from the patient plate. Typically the foils 38 and 40 of the tongue 36 are separated by an insulating substrate 42. The tongue is relatively flat and flexible, as a result of its construction. The remaining portion of the patient plate is of considerably greater conductive surface area than that of the tongue 36.

The tongue conductor 36 is inserted within a passageway 44 defined by a housing 46 of the connector 20. A lever member 48 is connected within the connector 20 to pivot with respect to the housing 46. When the lever 48 is pivoted to its closed position as illustrated in FIG. 2, the tongue conductor 36 is mechanically retained and gripped within the passageway 44. When the lever 48 is pivoted to its open position as is illustrated in FIG. 3, the mechanical retention of the tongue conductor is released and the tongue conductor can be easily withdrawn from the connector 20.

By comparing FIGS. 2 and 3, it can be seen that the lever 48 fits within a recess 50 formed in the housing 46, when the lever 48 is in the closed position. The upper surface of the lever is smooth and flat and the upper surface of the housing 46 adjacent to the lever 48 is also smooth and flat to create a continuous upper smooth surface of the connector 20 when the lever is closed. The housing 46 and lever 48 define a generally flat, compact and relatively rectangularly shaped structure of the connector 20. The relatively flat rectangular shape with the flat smooth upper surface allows the connector 20 to be positioned underneath the patient if desired without creating injury.

The internal elements of the connector 20 are illustrated in FIGS. 4 and 5. The housing 6 includes an upper housing portion 46a and a lower housing portion 46b. Posts 52 extend upward from the lower housing portion 46b into apertures 54 formed in the upper housing portion 46a. The posts 52 are welded into the apertures 54 to hold the housing portions 46a and 46b together into the integral housing assembly 46. The retention of the housing portions in the manner described also retains all of the other internal elements of the connector 20. The assembly of the upper and lower housing portions in the manner described provides a housing 46 of a relatively rigid structure which is not subject to flexibility or distortion by the forces induced during use. The housing portions 46a and 46b are preferably formed of electrically insulating plastic material.

A pair of spaced apart lower electrical contact means or members 56a and 56b are positioned on the lower housing portion 46b. Each of the lower contacts 56a includes a major portion of generally flat rectangularly shaped configuration. The rectangular shape has its longer dimension in a longitudinal sense, and this dimension extends in the passageway 44 (FIG. 8) generally in the longitudinal direction in which the tongue portion of the patient plate is inserted into and withdrawn from the connector 20. A forward edge 5 of each lower contact 56a and 56b is bent downward and fits within a slot 60 (FIG. 6) formed in the lower housing portion 46b. The rear edge of each lower contact 56a and 56b includes a middle extension 62 extending to the rear and two transverse edges 64 which are downturned to fit within slots 66 (FIG. 6) in the lower housing member 46b. As is shown in FIG. 4, the middle extension 62 of each lower contact 56a and 56b is respectively electrically conneoted to the return cable conductors 34a and 34b as for exampled by soldering or crimping. As is shown in FIG. 6, a generally elongated rectangular recess 68 is formed in the lower housing portion 46 for the purpose of receiving each lower contact. Once received in the recess 68, each lower contact generally extends along the lower marginal area of the passageway at the upper marginal area of the lower housing portion 46b, as is illustrated in FIGS. 8 and 12.

Each middle extension 62 of the lower contacts extends into a chamber 70a formed in the lower housing portion 46b. A slot 72a extends from the rear end of the lower housing portion and includes teeth 74a. As is shown in FIG. 5, a generally complementarily shaped chamber 70b, slot 72b and teeth 74b are formed in the upper housing portion 46a to align with those corresponding elements in the lower housing portion 46b. The space provided by the chambers 70a and 70b allows the cable conductors 34a and 34b to be attached to the middle extension 62. The slots 72a and 72b and the teeth 74a and 74b grip the outside of the return conductor 34 when the housing portions 46a and 46b are connected together, thereby retaining the end of the return cable within the conductor 20.

Near the midpoint along the longitudinal extension of each lower contact 56a and 56b, an aperture 76 is formed through the lower contact. As is shown in FIGS. 4 and 6, the aperture 76 is located above an indention 78 formed in the recess 68 in the lower housing portion 46. The aperture 76 and the indention 78 thus form an indention or recess in the lower marginal area of the passageway 44. This indention, as will be described below, is useful in mechanically retaining the tongue portion within the connector 20.

Extending transversely outward from each of the lower contacts 56a and 56b is a tab 80a and 80b, respectively. The tabs 80a and 80b are on transversely opposite sides of the passageway. The tabs 80a and 80b extend generally vertically with respect to the flat horizontal surface of the lower contacts. A hole 82 is formed through each of the tabs 80a and 80b. As is shown in FIG. 6, side recesses 84 extend from the sides of the recesses 68 to receive portions of the tabs 80a and 80b. As is shown in FIG. 5, slot receptacles 86 are formed in the upper housing portion 46a to align with the tabs 80a and 80b and to retain the upper ends of the tabs when the housing portions 46a and 46b are connected together.

The lower contacts 56a and 56b are retained rigidly within the connector as a result of mechanically connecting the housing portions 46a and 46b. The lower contacts 56a and 56b are prevented from moving longitudinally in the passageway by the downturned front and rear edges 58 and 64 which are received within the slots 60 and 66, respectively. Vertical movement of the lower contacts 56a and 56b is prevented as a result of the retention force from the slot receptacles 86 in the upper housing portion 46a. Thus, the lower contacts 56a and 56b are assembled and retained in the connector 20 very easily simply by positioning them on the lower housing portion 46b and mechanically connecting the upper housing portion 46a.

The lever member 48 is generally of an L shaped configuration when viewed in a plane perpendicular to its pivot axis. as shown in FIGS. 9 and 11. The lever member includes a longer leg portion 48a which is that portion which is gripped and manipulated during operation of the connector. A shorter leg portion 48b extends inward of the connector from the longer leg portion 48a at the inner pivoted end of the lever 48. A hole 88 is formed in the recess 50 in order that the shorter leg portion 48b extend into the passageway within the connector. The lever 48 comprises, and is preferably formed entirely of electrically insulating material.

A pair of upper electrical contact means or members 90a and 90b are positioned on the lever leg portion 48b. The upper contacts 90a and 90b are positioned on the lever member in a spaced apart and electrically insulated relationship. In the embodiment shown in FIGS. 4 through 12, each of the upper contacts 90a and 90b is formed generally of a triangular shaped configuration. The upper contacts 90a and 90b are received respectively in recesses 92a and 92b formed in the shorter leg portion 48b. The upper contacts 90a and 90b are held in the recesses 92 by pivot pins 94a and 94b respectively. The pivot pins 94a and 94b extend through insulating material in the leg portions 48b on each transverse side of the contacts 90a and 90b. The pivot pins thus retain the upper contacts to the lever in a mechanical sense, and cause the electrical contacts to move with the lever when it is pivoted. The generally triangular shaped upper contacts 90a and 90b conform with the general shape of the leg portion 48b.

The pivot pins 94a and 94b and the tabs 80a and 80b, respectively, with their apertures 82, comprise portions of a hinge structure or means operative for piVotably connecting the lever member 48 at the connector 20. The pivot pins 94a and 94b fit within the apertures 82. Since the lower contacts 56a and 56b the tabs 80a and 80b, the pivot pins 94a and 94b, and the upper contacts 90a and 90b, are all formed of metallic electrically conductive material, the hinge structure both mechanically and electrically connects the upper contacts 90a and 90b with the lower contacts 56a and 56b. Because of the insulating relationship of the upper contacts 90a and 90b from one another in the lever 48. and the insulating relationship of the lower contacts 56a and 56b from one another on the lower housing portion 46b, the upper contact 90a is electrically connected only to the lower contact 56a, and the other upper contact 90b is electrically connected only to the other lower contact 56b.

The separate electrical connection of one of the upper contacts with one of the lower contacts achieves the improved feature that an electrical connection will be made with either the upper foil 38 or lower foil 40 of the tongue portion 36 (FIGS. 2 and 3). Should either the upper conductive foil 38 or the lower conductive foil 40 fail in its electrical connection to the main conductive surface portron of the patient plate, electrical energy will still be transferred through the other conductive foil. Furthermore, the sensing current between the conductive foils at the two spaced apart locations is maintained should either of the conductive foils fail.

The separately electrically connected pairs of upper and lower contacts also allow the connector 20 to be used with the type of patient plate which provides only one conductive foil on its tongue portion. Patient plates with single conductive foils on the tongue portion can be inserted into the connector 20 with the conductive foil either upward or downward. Again, the separately electrically connected upper and lower contacts achieve the advantage that no particular specific orientation of the patient plate must be accommodate when it is inserted into the connector.

The lever member 48 also includes retention means for contacting and mechanically retaining the tongue portion of the patient plate within the housing. The retention means is preferably the lever leg portion 48b which extends into the passageway 44 when the lever is in the closed position, as is shown in FIG. 9. The curved surface point on the shorter leg portion 48b at the greatest distance the pivot pin 94a deforms the tongue conductor downward into the recess defined by the aperture 76 in each of the lower contacts and the ignition 78 formed into the lower housing portion 46b below each aperture 7. A mechanical advantage is achieved by moving the longer leg portion 48a to deform the tongue conductor portion into this recess. In deforming the tongue conductor by bending it downward into the aperture 76 and indention 78, the bend creates a resistance which resists the withdrawal of the tongue portion from the passageway 44. The resistance created by deforming the tongue portion also induces a vertical force at the outermost point of the leg portion 48a spaced away from the pivot pin. The location of this vertical force is off of (to the right as shown in FIG. 9) of the pivot pin axis. This upward force thus tends to hold the lever member in the closed position, because the upward force induces a torque on the lever member which keeps it within the recess 50. This off center pivot force induced by deforming the tongue portion conveniently creates a force for keeping the lever in the closed position, without requiring additional internal mechanical elements to accomplish such a function. In order to overcome the off center pivot force, the longer leg portion 48a must be moved toward the open position until the outermost point on the shorter leg portion 48b spaced away from the pivot pin axis is directly below or to the left of (as shown in FIG. 9) a plane from the outermost point through the pivot pin.

Because the external surface contour of the upper contacts 90a and 90b generally conforms with that surface contour of the portion of the lever member defining the other parts of the shorter leg portion 48b, the upper contacts preferably become a portion of the retention means. However, the upper contacts could be made separately of the retention means. In fact, as shown in FIG. 5, the portion of the lever member leg portion 48b on each transverse side of the slot 92 also operates to deform the tongue portion into the indention and retain it as is shown in FIG. 9.

Another advantage of the retention means as provided in the connector 20 can be better understood from FIG. 8. Because of the clearance between the furthermost end of the shorter leg portion 48b and the recess defined by the aperture 76 and indention 78, there is no force tending to restrain the free pivoting of the lever until the tongue portion 36 is positioned therebetween. Thus, the proper mechanical and hence electrical connection to the tongue portion can be sensed upon closing the lever member.

An alternative arrangement for certain elements of the electrical connector 20 is illustrated in FIGS. 13, 14 and 15. In this alternative arrangement, single bent wires 100a and 100b achieve the functions of the pivot pins, the upper electrical contacts, and the retention means. As can be seen in FIG. 14, the upper bent wires 100a and 100b have a first outer end 102 which fits within the aperture 82 of the tabs 80a and 80b. An inner end 104 extends generally perpendicular to the outer end 102. The inner end 104 of each wire 100a and 100b is received within a hole 106 which extends generally perpendicular to the pivot axis of the lever 48'. The middle portion of each wire 100a and 100b, between the inner end 102 and the outer end 104, extends generally parallel to the pivot axis and includes a bend projection portion 108. The bend projection 108 is intended to align with and extend into the aperture 76 in each lower contact when the lever is in the closed position. The curved point surface of the bend projection 108 contacts the tongue portion, deforms it, and creates the mechanical force for restraining the tongue portion against withdrawal from the passageway 44. A groove 110 extends from the hole 104 in the shorter leg portion 48b' of the lever 48' in order to receive the portions 102 and 108 of the bent wire contacts 100a and 100b. The orientation and alignment of the bent wire contacts 100a and 100b in the shorter leg portion 48b' can provide an off center pivoting arrangement similar to that provided by the arrangement shown in the embodiments of FIGS. 8 to 12. However, the particular orientation illustrated in FIGS. 13, 14 and 15 does not provide the off center pivoting arrangement because the bent wire portion 108 is located directly vertically below the pivot axis when the lever 48' is in the closed position as is shown in FIG. 13. Depending upon the type, flexibility and characteristics of the tongue portion of the conductor, the off center pivoting arrangement may not be necessary, since adequate retention force might be obtained without the off center pivoting arrangement. It should be noted that whether or not the off center pivoting arrangement is provided, any forced withdrawal of the tongue portion out of the passageway 44 induces a torque on the lever which tends to maintain it in the closed position. This torque is induced as a result of the deflection of the tongue portion into the recess defined by the aperture 76 and indention 78. Thus, even if an off center pivoting arrangement is not provided, good retention force for resisting the accidental forces separation of the tongue portion from the connector is achieved.

In both of the embodiments illustrated, the upper contacts are assembled into the lever member by simple mechanical insertion. The lever member is next pivotably connected to the tabs 80a and 80b of the lower contacts 56a and 56b, respectively. The upper housing portion 46a is next attached to the lower housing portion 46b by inserting the longer lever leg 48a or 48a' through the hole 88 in the recess 50 in the upper housing portion. The posts 52 are permanently connected into the apertures 54 to retain the housing portions together. With the upper and lower housing portions mechanically connected together, all of the internal elements of the connector 20 are retained in position.

Another substantial advantage of the connector 20 is that the mechanical and electrical interrelationship, through the hinge structure, of the upper and lower contacts avoids substantial reliance on the housing to establish the mechanical fit and clearance between the upper and lower contacts. As is seen from the hinge structure, a rigid mechanical pivoting connection is created between the upper and lower contacts. Thus, if the flexibility of the plastic housing increases from use, the greater flexibility has no effect on the mechanical fit and contact of the upper and lower contacts. This is a substantial advantage compared to certain other prior connectors which must rely on the rigidity of the housing. In such prior connectors, the flexibility of the housing increases with use and age, and ultimately intermittent electrical contact with the foils of the tongue portion may result. Of course, an intermittent electrical contact can increase the possibility and chances for earth ground leakage paths for the high frequency electrical current, thus increasing the risks of undesirable patient injury and burns.

In both embodiments of the electrical connector described herein, it can be seen that the electrical contacts are positioned well within the interior of the connector when the lever is closed. No gaps and spaces for current paths from the patient to the internal elements exist through which potentially high density currents could flow, thus bypassing the larger conductive surface of the patient plate. The risks for patient burns due to such bypass currents are therefore reduced.

The nature, operation and improvements available from two embodiments of the present invention have been shown and described with a degree of specificity. It should be understood, however, that the specificity of this description has been made by way of preferred example and that the invention is defined by the scope of the appended claims.

The invention claimed:

1. An electrical connector for establishing a selective electrical connection to a tongue-like conductor, comprising:
   a housing comprising electrical insulating material and defining a passageway extending from the exterior to the interior of the housing into which the tongue conductor is inserted;
   a lever member comprising electrical insulating material and connected for pivoting with respect to the housing between opened and closed positions, the lever member including a leg portion which moves in an arcuate path into the passageway when the lever member is pivoted into the closed position;
   retention means for contacting and mechanically retaining the tongue conductor within the housing, said retention means positioned on and pivotably carried by the leg portion of the lever member into the passageway for directly mechanically contacting and retaining the tongue conductor when the lever member is in the closed position and to withdraw for releasing the mechanical retention of the tongue conductor within the passageway when the lever member is in the open position;
   a pair of lower electrical contact means retained within the housing in a spacially separated and electrically insulated relationship at a lower location in the passageway, each lower contact means electrically contacting the lower surface of the tongue conductor at spacially separated locations;
   a pair of upper electrical contact means connected to the lever member in a spacially separated and electrically insulated relationship, each upper contact means located on the lever member at a predetermined location to be pivotably carried toward and oriented above the lower contact means upon pivoting of the lever member into the closed position, each upper contact means operatively electrically contacting the upper surface of the tongue conductor at spaced apart locations when the lever member is in the closed position; and
   means within the housing for electrically connecting one of the upper contact means with one of the lower contact means.

2. An electrical connector for establising a selective electrical connection from an electrical cable conductor to a tongue-like conductor, comprising:
   a housing comprising electrical insulating material and defining a passageway extending from the exterior to the interior of the housing into which the tongue conductor is inserted;
   a lever member comprising electrical insulating material and connected for pivoting with respect to the housing between opened and closed positions, the lever member including a leg portion which moved in an arcuate path into the passageway when the lever member is pivoted into the closed position;
   retention means for contacting and mechanically retaining the tongue conductor within the housing, said retention means positioned on and pivotably carried by the leg portion of the lever member into the passageway for directly mechanically contacting and retaining the tongue conductor when the lever member is in the closed position and to withdraw for releasing the mechanical retention of the conductor within the passageway when the lever member is in the open position;

a pair of upper electrical contact means connected to the leg portion of the lever member in a spacially separated and electrically insulated relationship, each upper contact means having a contour including a point-like surface for projecting into the passageway and for directly electrically contacting the upper surface of the tongue conductor at spaced apart locations when the lever member is in the closed position;

means within the housing for separately electrically connecting each of the upper contact means to the electrical cable conductor by which electrical current is conducted between the upper contact means and the tongue conductor.

3. An electrical connector for establising a selective electrical connection from an electrical cable conductor to a tongue-like conductor, comprising:

a housing comprising electrical insulating material and defining a passageway extending from the exterior to the interior of the housing into which the tongue conductor is inserted;

a lever member comprising electrical insulating material and connected for pivoting with respect to the housing between opened and closed positions;

retention means for contacting and mechanically retaining the tongue conductor within the housing, said retention means operatively connected to the lever member and having at least one point-like surface for projecting into the passageway for directly mechanically contacting and retaining the tongue conductor when the lever member is in the closed position and to withdraw for releasing the mechanical retention of the tongue conductor within the passageway when the lever member is in the open position;

a pair of lower electrical contact means retained within the housing in a spacially separated and electrically insulated relationship at a lower location in the passageway, each lower contact means electrically contacting the lower surface of the tongue conductor at spacially separated locations;

each lower contact means having an aperture formed therein at a location spaced transversely across the passageway from the point-like surface of the retention means;

the point-like surface of the retention means operatively bending the tongue conductor into each aperture to create a resistance to the withdrawal of the tongue conductor from the passageway when the lever member is in the closed position; and means within the housing for electrically connecting the lower contact means to the electrical cable conductor by which electrical current is conducted between the lower contact means and the tongue conductor.

4. An electrical connector as defined in claims 1, 2 or 3 wherein the upper surfaces of the lever member and the housing define a generally continuous upper surface of the connector when the lever member is in the closed position.

5. An electrical connector as defined in claims 1, 2 or 3 wherein the housing defines a recess in its upper surface in which the lever member rests when in the closed position, and the upper surface of the lever member and the upper surface of the housing adjoining the lever member generally define a flat upper surface of the connector when the lever member is in the closed position.

6. An electrical connection as defined in claim 1 wherein the upper contact means is positioned on the leg portion of the lever member.

7. An electrical connector as defined in claims 1 or 2 further comprising:

means within the housing defining at least one indention located at the lower marginal area of the passageway, and wherein:

the retention means extends into the passageway from an upper marginal area of the passageway at a location transversely spaced across the passageway from the indention, and the retention means operatively bends the tongue conductor into the indention to create a resistance to the withdrawal of the tongue conductor from the passageway when the lever member is in the closed position.

8. An electrical connector as defined in claim 7 wherein the lever member is generally L shaped to define a shorter leg portion and a longer leg portion, the shorter leg portion being the aforesaid leg portion which moves in an arcuate path into the passageway when the lever member is moved to the closed position, the shorter leg portion including the retention means, and the deformation of the tongue conductor by the retention means into the indention induces an off center pivot force tending to hold the lever member in the closed position when the tongue conductor is retained in the connector.

9. An electrical connector as defined in claim 8 wherein the indention and the off center pivot force induced on the lever member are located relative to the pivot axis of the lever member to tend to induce greater off center pivot force upon removal of the tongue conductor from the passageway when the lever member is in the closed position.

10. An electrical conductor as defined in claim 1 further comprising:

means within the housing for electrically connecting the other of the upper contact means with the other of the lower contact means separately of the electrical connection of the one upper and one lower contact means.

11. An electrical conductor for establishing a selective electrical connection to a tongue-like conductor, comprising:

a housing comprising electrical insulating material and defining a passageway extending from the exterior to the insulator of the housing into which the tongue conductor is inserted;

a lever member comprising electrical insulating material and connected for pivoting with respect to the housing between opened and closed positions;

retention means for contacting and mechanically retaining the tongue conductor within the housing, said retention means operatively connected to the lever member to extend into the passageway for mechanically contacting and retaining the tongue conductor when the lever member is in the closed position and to withdraw for releasing the mechanical retention of the tongue conductor within the passageway when the lever member is in the open position;

a pair of lower electrical contact means retained within the housing in a spacially separated and electrically insulated relationship at a lower location in the passageway, each lower contact means electrically contacting the lower surface of the tongue conductor at spacially separated locations;

a pair of upper electrical contact means connected to the lever member in a spacially separated and electrically insulated relationship, each upper contact means located on the lever member at a predetermined location to be carried toward and oriented above the lower contact means upon pivoting of the lever member into the closed position, each upper contact means operatively electrically contacting the upper surface of the tongue conductor at spaced apart locations when the lever member is in the closed position;

means within the housing for electrically connecting one of the upper contact means with one of the lower contact means; and said lever member is mechanically pivotably connected at the housing by a hinge structure, the hinge structure comprises electrically conductive elements, and the means electrically connecting the upper and lower contact means comprises the hinge structure.

12. An electrical connector for establishing a selective electrical connection to a tongue-like conductor, comprising:

a housing comprising electrical insulating material and defining a passageway extending from the exterior to the interior of the housing into which the tongue conductor is inserted;

a lever member comprising electrical insulating material and connected for pivoting with respect to the housing between opened and closed positions;

retention means for contacting and mechanically retaining the tongue conductor within the housing, said retention means operatively connected to the lever member to extend into the passageway for mechanically contacting and retaining the tongue conductor when the lever member is in the closed position and to withdraw for releasing the mechanical retention of the tongue conductor within the passageway when the lever member is in the open position;

a pair of lower electrical contact means retained within the housing in a spacially separated and electrically insulated relationship at a lower location in the passageway, each lower contact means electrically contacting the lower surface of the tongue conductor at spacially separated locations;

a pair of upper electrical contact means connected to the lever member in a spacially separated and electrically insulated relationship, each upper contact means located on the lever member at a predetermined location to be carried toward and oriented above the lower contact means upon pivoting of the lever member into the closed position, each upper contact means operatively electrically contacting the upper surface of the tongue conductor at spaced apart locations when the lever member is in the closed position; and wherein said lever member is mechanically pivotably connected at the housing by a hinge structure, and the hinge structure comprises a tab mechanically and electrically connected to one of the upper or the lower contact means, a pin mechanically and electrically connected to the other one of the one upper or one lower contact means, and the pin also mechanically pivotably connecting the lever member at the tab.

13. An electrical connector for establishing a selective electrical connection to a tongue-like conductor, comprising:

a housing comprising electrical insulating material and defining a passageway extending from the exterior to the interior of the housing into which the tongue conductor is inserted;

a lever member comprising electrical insulating material and connected for pivoting with respect to the housing between opened and closed positions;

retention means for contacting and mechanically retaining the tongue conductor within the housing, said retention means operatively connected to the lever member to extend into the passageway for mechanically contacting and retaining the tongue conductor when the lever member is in the closed position and to withdraw for releasing the mechanical retention of the tongue conductor within the passageway when the lever member is in the open position;

a pair of lower electrical contact means retained within the housing in a spacially separated and electrically insulated relationship at a lower location in the passageway, each lower contact means electrically contacting the lower surface of the tongue conductor at spacially separated locations;

a pair of upper electrical contact means connected to the lever member in a spacially separated and electrically insulated relationship, each upper contact means located on the lever member at a predetermined location to be carried toward and oriented above the lower contact means upon pivoting of the lever member into the closed position, each upper contact means operatively electrically contacting the upper surface of the tongue conductor at spaced apart locations when the lever member is in the closed position; and wherein:

each of the lower contact means is generally formed as a flat plate-like member;

each flat plate-like member defines an aperture therein, the aperture defines at least in part an indention located in the lower marginal area of the passageway at a location generally vertically spaced from the location at which the upper contact means extends into the passageway when the lever member is in the closed position; and the lever member is pivotably connected at the housing by a hinge structure located at each transverse side of the passageway, each hinge structure including means mechanically and electrically connecting each lower plate-like contact means with the upper contact means located vertically above the aperture.

14. An electrical connector as defined in claim 13 wherein the hinge structure further comprises:

a tab mechanically and electrically connected to and extending transversely away from each lower plate-like contact means, the tabs of both lower plate-like means extending transversely on opposite sides of the passageway in the connector;

a pivot pin extending on each transverse opposite side of the lever member and operative for defining a pivot axis about which the lever member pivots;

at least one pivot pin being electrically and mechanically connected to the upper contact means; and at least one pivot pin being pivotally connected mechanically and electrically to the tab.

15. An electrical connector as defined in claim 14 wherein the upper contact means is substantially mechanically rigidly connected to the pivot pin.

16. An electrical connector as defined in claim 3 wherein the lever member is generally L shaped to define a shorter leg portion and a longer leg portion, the shorter leg portion moves in an arc into the passageway when the lever member is moved to the closed position, the shorter leg portion including the retention means, and the deformation of the tongue conductor by the retention means into the aperture induces an off center pivot force tending to hold the lever closed when the tongue conductor is retained in the connector.

17. An electrical connector as defined in claim 16 wherein the aperture and the off center pivot force induced on the lever member are located relative to the pivot axis of the lever member to tend to induce greater off center pivot force upon removal of the tongue conductor from the passageway when the lever member is in the closed position.

* * * * *